US008975096B2

United States Patent
Kim et al.

(10) Patent No.: US 8,975,096 B2
(45) Date of Patent: Mar. 10, 2015

(54) JIG, MANUFACTURING METHOD THEREOF, AND FLIP CHIP BONDING METHOD FOR CHIPS OF ULTRASOUND PROBE USING JIG

(71) Applicants: Samsung Electronics Co., Ltd., Suwon-si (KR); Kyungpook National University Industry-Academic Cooperation Foundation, Daegu (KR)

(72) Inventors: Young Il Kim, Suwon-si (KR); Bae Hyung Kim, Yongin-si (KR); Jong Keun Song, Yongin-si (KR); Seung Heun Lee, Seoul (KR); Kyung Il Cho, Seoul (KR); Yong Rae Roh, Daegu (KR); Won Seok Lee, Daegu (KR)

(73) Assignees: Samsung Electronics Co., Ltd., Suwon-si (KR); Kyungpook National University Industry-Academic Cooperation Foundation, Daegu (KR)

(*) Notice: Subject to any disclaimer, the term of this patent is extended or adjusted under 35 U.S.C. 154(b) by 0 days.

(21) Appl. No.: 13/926,278

(22) Filed: Jun. 25, 2013

(65) Prior Publication Data
US 2013/0341303 A1    Dec. 26, 2013

(30) Foreign Application Priority Data

Jun. 25, 2012 (KR) .................. 10-2012-0068261

(51) Int. Cl.
G01R 31/26 (2014.01)
H01L 21/66 (2006.01)
A61B 8/00 (2006.01)
B06B 1/02 (2006.01)
H01L 23/00 (2006.01)

(52) U.S. Cl.
CPC ............ *A61B 8/4411* (2013.01); *B06B 1/0292* (2013.01); *H01L 24/75* (2013.01); *H01L 24/81* (2013.01); *H01L 2224/75983* (2013.01); *H01L 2224/75744* (2013.01); *H01L 2224/75745* (2013.01); *H01L 2224/81191* (2013.01); *H01L 2224/81815* (2013.01); *H01L 2224/7598* (2013.01); *H01L 2224/131* (2013.01); *H01L 2224/16238* (2013.01)
USPC ................... 438/14; 438/17; 438/33; 438/53; 73/41; 73/579; 73/597; 73/862

(58) Field of Classification Search
None
See application file for complete search history.

(56) References Cited

U.S. PATENT DOCUMENTS

| 6,854,338 | B2* | 2/2005 | Khuri-Yakub et al. .... 73/861.27 |
| 7,305,883 | B2 | 12/2007 | Khuri-Yakub et al. |
| 7,741,686 | B2* | 6/2010 | Khuri-Yakub et al. ....... 257/416 |
| 8,119,426 | B2 | 2/2012 | Kobayashi et al. |
| 8,345,508 | B2 | 1/2013 | Wodnicki et al. |

(Continued)

FOREIGN PATENT DOCUMENTS

| JP | 2009-511880 A | 3/2009 |
| KR | 10-2011-0031406 A | 3/2011 |

*Primary Examiner* — Duy Deo
(74) *Attorney, Agent, or Firm* — Sughrue Mion, PLLC

(57) ABSTRACT

A jig includes a wafer including an accommodation groove configured to accommodate a capacitive micromachined ultrasonic transducer (cMUT) when flip chip bonding is performed, and a separation groove formed in a bottom surface of the accommodation groove, the separation groove having a bottom surface that is spaced apart from thin films of the cMUT that face the bottom surface of the separation groove when the cMUT is seated on portions of the bottom surface of the accommodation groove.

12 Claims, 25 Drawing Sheets

(56) References Cited

U.S. PATENT DOCUMENTS

| | | |
|---|---|---|
| 2007/0089516 A1 | 4/2007 | Khuri-Yakub et al. |
| 2011/0071397 A1 | 3/2011 | Wodnicki et al. |
| 2013/0146995 A1* | 6/2013 | Chen .............................. 257/416 |
| 2013/0289410 A1* | 10/2013 | Cho et al. ....................... 600/459 |

* cited by examiner

JIG, MANUFACTURING METHOD THEREOF, AND FLIP CHIP BONDING METHOD FOR CHIPS OF ULTRASOUND PROBE USING JIG

CROSS-REFERENCE TO RELATED APPLICATION

This application claims priority from Korean Patent Application No. 2012-0068261, filed on Jun. 25, 2012 in the Korean Intellectual Property Office, the disclosure of which is incorporated herein by reference.

BACKGROUND

1. Field

Embodiments of the present disclosure relate to flip chip bonding of chips constituting an ultrasound probe.

2. Description of the Related Art

Ultrasound diagnostic devices operate to obtain a cross-sectional image of a soft tissue or bloodstream in a non-invasive manner by irradiating an ultrasound signal through the surface of a subject to a target site inside the subject and receiving an ultrasound echo signal reflected from the target site.

The ultrasound diagnostic devices are smaller in size and less expensive than other image diagnostic devices (e.g., X-ray diagnostic device, computerized tomography (CT) scanner, magnetic resonance imaging (MRI), nuclear medicine diagnostic device, etc.). In addition, the ultrasound diagnostic devices may enable real-time display of a diagnostic image and are safe because there is no risk of exposure to X-rays. Thus, these ultrasound diagnostic devices are widely used in diagnosis in obstetrics and gynecology, diagnosis for the heart and abdomen, and urology diagnosis.

An ultrasonic diagnostic device includes an ultrasound probe to transmit an ultrasound signal to a subject and receive an ultrasound echo signal reflected from the subject to obtain an ultrasound image of the subject.

In general, the ultrasound probe includes an ultrasound transducer in which a plurality of piezoelectric crystal elements (i.e., piezoelectric vibrators) are arranged on a plane in a matrix or array form, and the piezoelectric crystal elements perform an interactive conversion between electric energy and mechanical vibration energy to transmit and receive an ultrasound signal.

Recently, a new concept of a non-contact ultrasound transducer, i.e., a capacitive micromachined ultrasonic transducer (cMUT) has been developed, which enables high-efficient transmission and receipt of an ultrasound.

The cMUT is a relatively new type of an ultrasound transducer that transmits and receives an ultrasound using vibration of hundreds of or thousands of micromachined thin films, and is manufactured based on micro electro mechanical systems (MEMS) technology. When thin films having a thickness of thousands of Å are formed on a semiconductor substrate used in a general semiconductor manufacturing process with being separated from each other with an air gap having a thickness of thousands of Å, the semiconductor substrate and the thin films form a capacitor with the air gap formed therebetween.

When alternating current flows to the manufactured capacitor, the thin films are vibrated and, consequently, an ultrasound is generated. By contrast, when the thin films are vibrated by an external ultrasound, a capacitance of the capacitor is changed and the change in capacitance of the capacitor is detected, thereby receiving an ultrasound.

A single cMUT has a diameter of only tens of micrometers and thus, even though ten thousands of cMUTs are arranged, the size thereof is only several millimeters. In addition, ten thousands of sensors may be accurately arranged at a desired position simultaneously using a one-time manufacturing process and thus the accuracy is incomparably superior to an array sensor using a piezoelectric sensor.

To transmit an electric signal to these cMUTs, the cMUTs need to be connected to an integrated circuit such as an application specific integrated circuit (ASIC) using a chip bonding method such as flip chip bonding.

Flip chip bonding is a technology by which solder balls (solder bumps) are formed on a semiconductor chip on which an integrated circuit is formed, to be electrically connected to the integrated circuit, and the semiconductor chip is directly mounted on a substrate using the solder balls. The flip chip bonding process may enable mounting of a semiconductor chip using solder balls and electrical connection through the solder balls and provide a short electrical path, and thus may be widely used in manufacturing electronic products that require miniaturization, light weight, and high-density mounting.

FIGS. 1A and 1B are diagrams for explaining a general flop chip bonding process.

To perform flop chip bonding of two chips, first, as illustrated in FIG. 1A, a surface of a first chip 10 on which bonding pads 12 are not formed is suctioned using a vacuum suction device 30 and a surface of a second chip 20 on which solder balls 22 are not formed is suctioned using a vacuum suction device 40 such that a surface of the first chip 10 on which the bonding pads 12 are formed faces a surface of the second chip 20 on which the solder balls 22 are formed. Subsequently, the solder balls 22 formed on the second chip 20 are dipped in a flux, and, as illustrated in FIG. 1B, the second chip 20 is pre-adhered to the first chip 10 by aligning the second chip 20 with the first chip 10 so that the solder balls 22 of the second chip 20 contact the bonding pads 12 of the first chip 10. Thereafter, the vacuum suction devices 30 and 40 that respectively suction the first and second suction devices 30 and 40 are removed and reflow treatment is performed thereon to adhere the solder balls 22 to the bonding pads 12, thereby completing flip chip bonding of the two chips.

FIG. 2 is a sectional view illustrating a structure of a cMUT 100.

As illustrated in FIG. 2, the cMUT 100 is manufactured by sequentially forming a lower electrode 120 and an insulating layer 130 on a semiconductor substrate 110 used in a general semiconductor manufacturing process, forming air gaps 140 on the insulating layer 130, and forming thin films 150 having a thickness of several to thousands of Å and an upper electrode (not shown because the thickness thereof is far smaller than that of the thin films 150) over the air gaps 140. In this regard, the semiconductor substrate 110 and the thin films 150 form a capacitor with the air gaps 140 formed therebetween. Each of the air gaps 140 is defined by a support member 160 made of a dielectric, and the thin films 150 supported by the support members 160 are formed over the respective air gaps 140. That is, the number of the thin films 150 corresponds to the number of the air gaps 140.

To electrically connect an integrated circuit such as an application-specific integrated circuit (ASIC) to cMUTs, a flip chip bonding technology, which is a core technology for packaging, may be applied. In the flip chip bonding process, there should be no problem with handling of chips, i.e., vacuum suction of chips.

To flip-chip bond a cMUT to an integrated circuit, bonding pads are formed on the side of a semiconductor substrate of the cMUT on which thin films are not formed, the surface of the cMUT on which the bonding pads are formed faces up, and the surface of the cMUT on which the thin films are formed faces down. The surface of the cMUT on which the thin films are formed is suctioned using a vacuum suction device to fix the cMUT, and the integrated circuit is aligned with the cMUT such that solder balls of the integrated circuit contact the bonding pads of the cMUT.

However, the thin films of the cMUT are very thin and thus are easily affected by external force. Thus, when vacuum pressure is applied to the thin films to suction the thin films in a flip chip bonding process, the thin films are easily damaged. That is, due to the characteristics of the thin films of the cMUT, it may not be possible to suction the surface of the cMUT on which the thin films are formed such that flip chip bonding may not be performed.

In addition, a generally used flip chip bonding technology is mainly bonding of chips in a one-to-one correspondence manner (bonding in a 1:1 manner). However, when at least two chips (chips B, C, . . . ) need to be bonded to a single chip A, the chip B is first bonded to the chip A, and then the remaining chips are consecutively bonded to the chip A one by one.

In this case, however, even though one of the cMUTs is first bonded to the integrated circuit in spite of damage to the thin films, it is difficult to bond the remaining cMUT(s) to the integrated circuit due to tilting of the bonded chip, resulting in reduced bonding accuracy. In addition, after bonding a single cMUT to the integrated circuit, it is difficult to perform flux dipping only on solder balls of the integrated circuit.

SUMMARY

One or more exemplary embodiments provide a jig, a manufacturing method thereof, and a method of performing flip chip bonding of chips for an ultrasound probe using the jig in which a jig to stably seat a semiconductor chip to be flip-chip bonded with a single semiconductor chip is manufactured, the semiconductor chip is seated at the jig, and then flip chip bonding is performed therebetween, and thus damage to the semiconductor chip including structures on opposite surfaces thereof which may be caused during flip chip bonding may be prevented.

One or more exemplary embodiments also provide a jig, a manufacturing method thereof, and a method of performing flip chip bonding of chips for an ultrasound probe using the jig in which a jig to stably seat a plurality of semiconductor chips to be flip-chip bonded with a single semiconductor chip is manufactured, the semiconductor chips are seated at the jig, and flip chip bonding is performed therebetween, and thus a degree of freedom of fabrication may be improved in bonding between the single semiconductor chip and the plurality of semiconductor chips (i.e., bonding may be possible to perform in a 1:n manner).

One or more exemplary embodiments also provide a jig, a manufacturing method thereof, and a method of performing flip chip bonding of chips for an ultrasound probe using the jig in which a jig to stably seat a semiconductor chip(s) to be flip-chip bonded with a single semiconductor chip is manufactured using a semiconductor manufacturing process, and thus bonding accuracy may be improved when flip chip bonding is performed between the semiconductor chips.

One or more exemplary embodiments also provide a jig, a manufacturing method thereof, and a method of performing flip chip bonding of chips for an ultrasound probe using the jig in which a jig including structures enabling bonding in a 1:1 or 1:n manner that are formed as an array is manufactured, a relatively large number of semiconductor chips are seated at the jig, alignment of a single semiconductor chip with the semiconductor chips is consecutively performed, and reflow treatment is performed once, and thus yield and throughput may be improved.

In accordance with an aspect of an exemplary embodiment, there is provided a jig including a wafer including an accommodation groove configured to accommodate a capacitive micromachined ultrasonic transducer (cMUT) when flip chip bonding is performed, and a separation groove formed in a bottom surface of the accommodation groove, the separation groove having a bottom surface that is spaced apart from thin films of the cMUT that face the bottom surface of the separation groove when the cMUT is seated on portions of the bottom surface of the accommodation groove.

The accommodation groove may have a first predetermined depth, and the separation groove may have a second predetermined depth from the bottom surface of the accommodation groove.

The accommodation groove may have a length and a width which are larger than a length and a width of the cMUT.

The separation groove may have a length and a width which are larger than a length and a width of a thin film forming region of the cMUT.

The jig may further include a tweezers loading area formed adjacent to the accommodation groove and configured to allow tweezers to pick up the cMUT when the cMUT is installed at the accommodation groove, wherein the tweezers loading area is formed in the wafer to have a third predetermined depth.

The wafer may be any one of a silicon (Si) wafer, a glass wafer, and a replica using the Si wafer or the glass wafer.

The jig may further include a plurality of vacuum holes formed below the separation groove and through which vacuum pressure is applied to the thin films of the cMUT when the flip chip bonding is performed.

In accordance with an aspect of another exemplary embodiment, there is provided a jig including a wafer including an accommodation groove configured to accommodate a capacitive micromachined ultrasonic transducer (cMUT) when flip chip bonding is performed; and seating ends provided in a bottom surface of the accommodation groove and configured to seat the cMUT within the accommodation groove so that thin films of the cMUT are spaced apart from and face an etched portion of the bottom surface of the accommodation groove face when the flip chip bonding is performed.

In accordance with an aspect of another exemplary embodiment, there is provided a jig including a wafer including accommodation grooves configured to accommodate a plurality of capacitive micromachined ultrasonic transducers (cMUTs) when flip chip bonding is performed; and a plurality of separation grooves formed bottom surfaces of the accommodation grooves, each of the separation grooves having a bottom surface that is spaced apart from thin films of a respective cMUT that face the bottom surface of the separation groove when the cMUTs are seated on portions of the bottom surfaces of the accommodation grooves.

In accordance with an aspect of another embodiment, there is provided a jig including an accommodation groove configured to accommodate a capacitive micromachined ultrasonic transducer (cMUT) when flip chip bonding is performed and a separation groove formed below the accommodation groove and configured to protect thin films of the cMUT.

The accommodation groove may have a first predetermined depth, and the separation groove may have a second predetermined depth from the bottom surface of the accommodation groove.

In accordance with an aspect of another embodiment, there is provided a jig including a wafer including an accommodation groove configured to accommodate an ultrasound transducer when flip chip bonding is performed; and a separation groove formed in a bottom surface of the accommodation groove, the separation groove having a bottom surface that is spaced apart from the ultrasound transducer when the ultrasound transducer is seated on portions of the bottom surface of the accommodation groove.

In accordance with an aspect of another embodiment, there is provided a method of manufacturing a jig, the method including performing first etching on a wafer to form an accommodation groove configured to accommodate a capacitive micromachined ultrasonic transducer (cMUT) when flip chip bonding is performed; and performing second etching on a portion of a bottom surface of the accommodation groove to form a separation groove having a bottom surface that is spaced apart from thin films of the cMUT that face the bottom surface of the separation groove when the cMUT is seated on portions of the bottom surface of the accommodation groove.

The first etching may include forming a first masking layer on an upper surface of the wafer to form the accommodation groove and etching the wafer to a first predetermined depth using the first masking layer as an etching blocking layer.

The second etching may include forming a second masking layer on the upper surface of the wafer on which the first etching has been performed and etching the wafer to a second predetermined depth using the second masking layer as the etching blocking layer.

The method may further include performing surface treatment to remove surface roughness of the accommodation groove and the separation groove formed after the first and second etching processes, wherein the surface treatment is any one of tetramethyl ammonium hydroxide (TMAH) dipping, KOH dipping, and plasma treatment.

The method may further include forming a plurality of vacuum holes through which vacuum pressure is applied to thin films of the cMUT when the flip chip bonding is performed, by performing third etching on the wafer.

The third etching may include forming a third masking layer on a lower surface of the wafer or on the upper surface of the wafer on which the second etching has been performed to form the vacuum holes having a certain length and a certain width and etching the wafer using the third masking layer as the etching blocking layer.

The first etching, the second etching, and the third etching may be performed by deep reactive-ion etching.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1A:
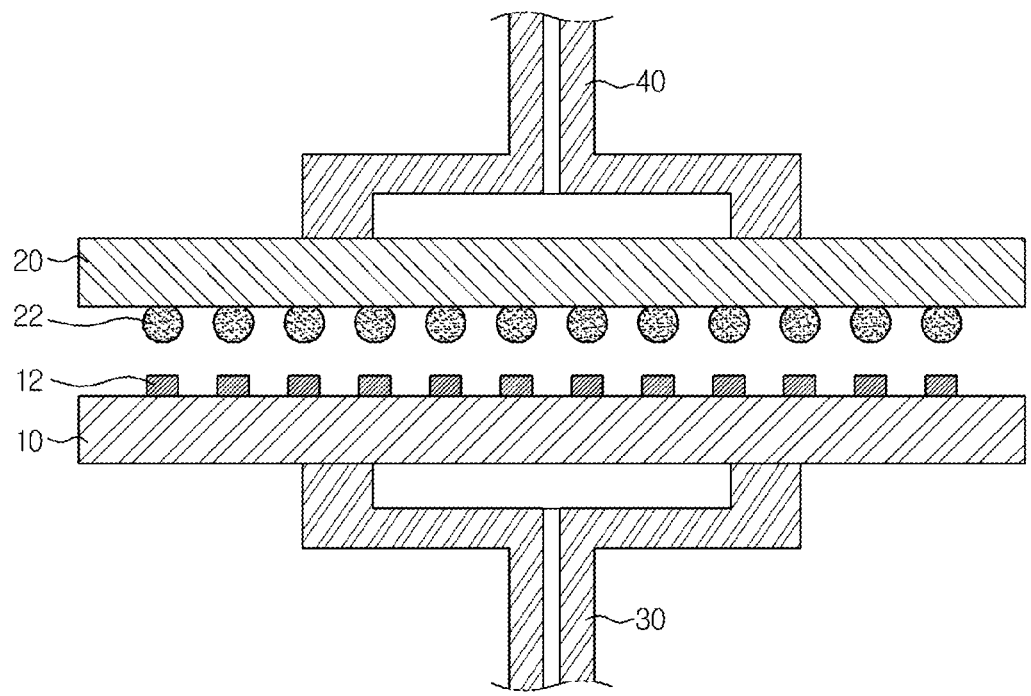
FIGS. 1A and 1B are diagrams for explaining a general flip chip bonding process.
Figure 1B:
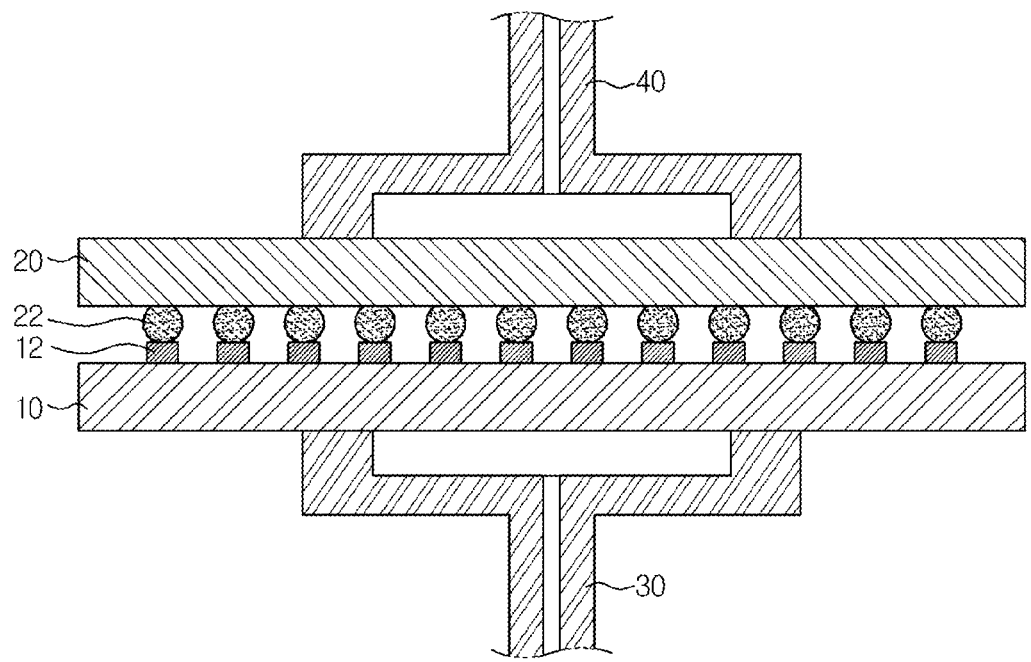
Figure 2:
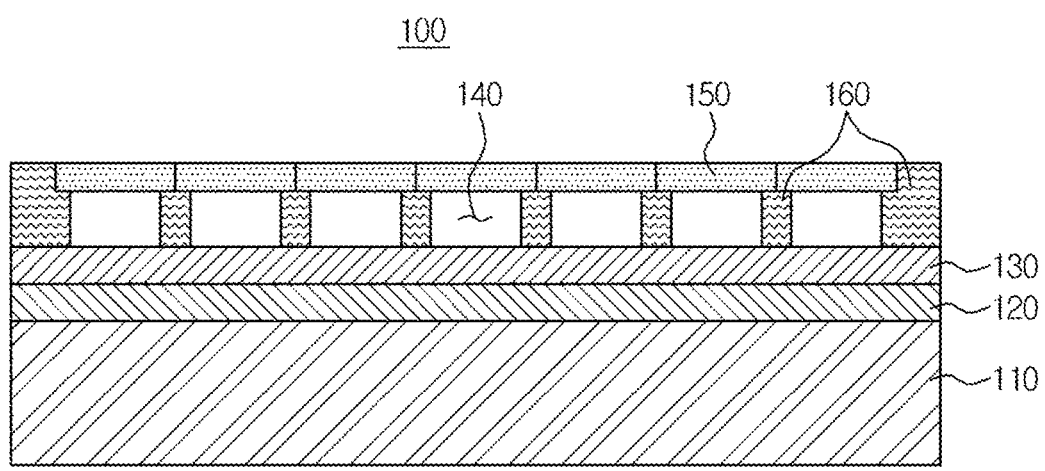
FIG. 2 is a sectional view illustrating a structure of a capacitive micromachined ultrasonic transducer (cMUT)

Hereinafter, embodiments will be described in detail with reference to the accompanying drawings in which like reference numerals refer to like elements throughout.

Figure 3A:
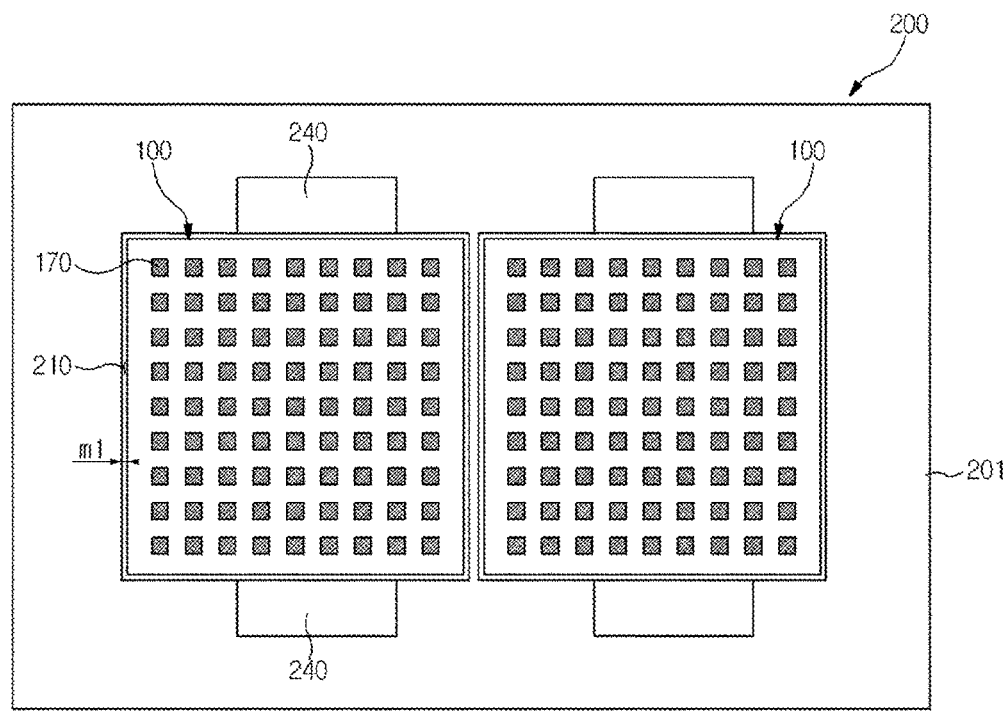
FIGS. 3A, 3B and 3C are diagrams for explaining a concept of a jig according to an embodiment.
Figure 3B:
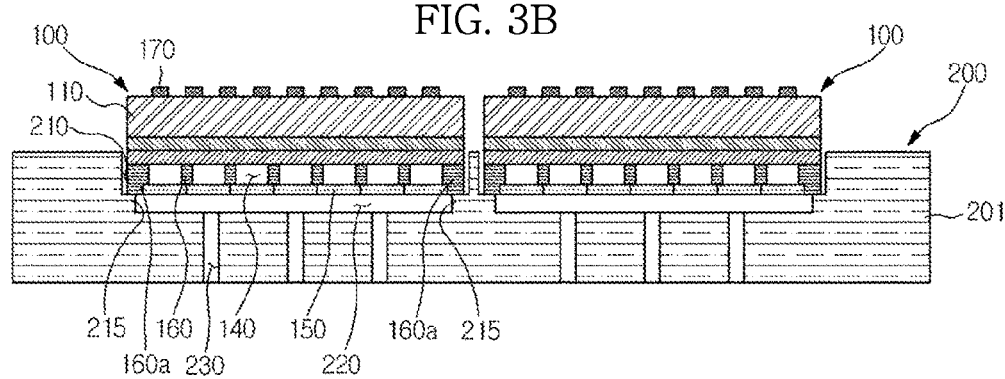
Figure 3C:
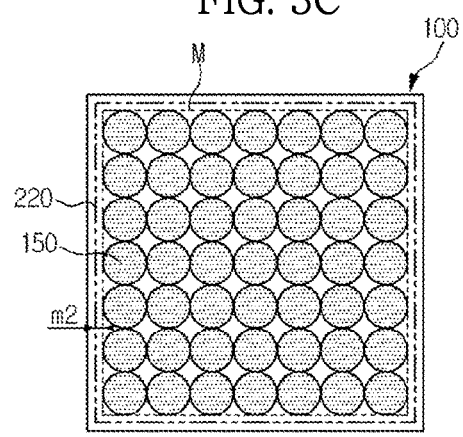

FIGS. 3A, 3B and 3C are diagrams for explaining a concept of a jig 200 according to an embodiment. In detail, FIG. 3A is a top view of a jig 200 according to an embodiment on which capacitive micromachined ultrasonic transducers (cMUTs) 100 are seated, FIG. 3B is a vertical sectional view of the jig 200 according to the embodiment on which the cMUTs 100 are seated, and FIG. 3C is a view illustrating a surface of the cMUT 100 on which thin films are formed.

To flip-chip bond a cMUT to an integrated circuit for transmission of an electrical signal to the cMUT, the cMUT needs to be fixed using a vacuum suction device upon the surface of the cMUT on which a thin film is formed. As described above, the thin film of the cMUT is very weak and thus, when vacuum pressure is directly applied to the thin film, the thin film may be easily damaged. Therefore, flip chip bonding may be difficult or impossible to implement. In addition, it is actually difficult to flip-chip bond at least two cMUTs to a single integrated circuit.

Therefore, in embodiments, without fixing the cMUT by directly applying vacuum pressure to the cMUT (in particular, a surface thereof on which a thin film is formed), which is a semiconductor chip subjected to flip chip bonding, a jig is configured to safely position the cMUT, the cMUT is seated on the jig, and vacuum pressure is applied to the micromachined jig, to fix the cMUT, followed by flip chip bonding. Therefore, damage to the cMUT by the vacuum pressure for suction may be prevented.

In addition, in the embodiments, a jig is configured to safely position n cMUTs (n=1, 2, ...), which are semiconductor chips subjected to flip chip bonding, and the cMUTs are seated on the jig, followed by flip chip bonding. Accordingly, it may be possible to perform flip chip bonding in a 1 to n manner. In the 1 to n manner, 1 denotes the number of a flip-chip bonded integrated circuit and n denotes the number of the flip-chip bonded cMUTs.

As illustrated in FIG. 3B, the jig 200 according to the embodiment may have a structure on which two cMUTs 100 are mounted. The jig 200 includes accommodation grooves 210 that are formed by etching a wafer 201 to a first determined depth d1 and respectively accommodate the cMUTs 100 during flip chip bonding and separation grooves 220 that are formed by etching an etched surface of the wafer 201 to a second predetermined depth d2 and are disposed below the accommodation grooves 210 to protect thin films 150 of each cMUT. In the present embodiment, the jig 200 includes two accommodation grooves 210 and two separation grooves 220 on which two cMUTs 100 are seated.

Each of the cMUTs 100 is provided with a plurality of bonding pads 170 on a surface on which the thin films 150 are not formed. The bonding pads 170 allow for electrical contact with solder balls formed in an integrated circuit. When flip chip bonding of the cMUTs 100 to the integrated circuit is performed, as illustrated in FIG. 3B, the cMUTs 100 are installed on the jig 200 such that the surface of each cMUT on which the bonding pads 170 are formed faces up and the surface of each cMUT on which the thin films 150 are formed faces down. That is, when flip chip bonding of the cMUTs 100 to the integrated circuit is performed, the cMUTs 100 are inserted into the respective accommodation grooves 210 such that the thin films 150 of each of the cMUTs 100 face a bottom surface of the separation groove 220, and each of the cMUTs 100 is seated on seating ends 215 formed during formation of the accommodation grooves 210 and the separation grooves 220 so that the thin films 150 of the cMUT 100 are spaced apart from the bottom surface of the separation groove 220.

As illustrated in FIG. 3B, among the accommodation grooves 210, the seating ends 215, and the separation grooves 220 formed at the jig 200, the accommodation grooves 210 and the seating ends 215 accommodate and support the cMUTs 100, that is, allow the cMUTs 100 to be seated on the jig 200, and the separation grooves 220 protect the thin films 150 of the cMUTs 100 which may be easily damaged by external force.

On the seating ends 215 formed due to a difference between widths of the accommodation groove 210 and the separation groove 220 are seated support members 160a formed at outermost portions of the cMUT 100 so that the cMUT 100 is situated on the jig 200. In addition, the thin films 150 of the cMUT 100 are spaced apart from the bottom surface of the separation groove 220 by an empty space (i.e., space of air) without contacting any structural element. Due to such structure of the jig 200, the thin films 150 of the cMUT 100, which are the weakest part, may be completely protected during flip chip bonding.

In addition, as illustrated in FIG. 3B, a plurality of vacuum holes 230, through which vacuum pressure is applied to the thin films 150 of the cMUT 100 during flip chip bonding, are formed below a region in which the cMUT 100 of the jig 200 is installed. Since the jig 200 includes the vacuum holes 230, vacuum pressure generated from a vacuum suction device is uniformly applied to the entire surface of the thin films 150 of the cMUT 100 through the vacuum holes 230. Thus, damage to the thin films 150 of the cMUT 100 due to direct contact between the thin films 150 of the cMUT 100 and the vacuum suction device may be prevented.

FIG. 3A is a top view of the jig 200 according to the embodiment on which the cMUTs 100 are seated. As illustrated in FIG. 3A, the jig 200 includes tweezers loading areas 240 that are disposed adjacent to the respective accommodation grooves 210 and allow tweezers with which the cMUTs 100 are picked up to be utilized when the cMUTs 100 are respectively installed at the accommodation grooves 210 of the jig 200. The tweezers loading areas 240 are formed by etching the wafer 201 to a third predetermined depth d3.

In addition, the length and width of the accommodation grooves 210 formed at the jig 200 have a first margin m1 (e.g., m1 is 5 to 10 μm) with respect to the length and width of the cMUTs 100 (here, the diameter of the cMUTs 100 when the cMUTs 100 have a circular shape), assuming that the cMUTs 100 generally have a rectangular shape. That is, the accommodation grooves 210 are provided such that a distance between side walls of the accommodation groove 210 and the cMUT 100 installed at the accommodation groove 210 ranges from 5 μm to 10 μm.

FIG. 3C is a view illustrating a surface of the cMUT 100 on which thin films 150 are formed. As illustrated in FIG. 3C, the thin films 150 are formed on a surface of the cMUT 100 on which the thin films 150 are to be formed, i.e., a lower surface of the cMUT 100 based on a direction in which the cMUT 100 is installed at the accommodation groove 210 of the jig 200, corresponding in number to the number of air gaps 140. In this regard, a region formed by connecting straight lines contacting edges of the thin films 150 arranged at the outermost among the plurality of thin films 150 is defined as a thin film forming region M. All the thin films 150 arranged at the cMUT 100 are included within the thin film forming region M.

In order that the thin films 150 of the cMUT 100 are present in an empty space without contacting any structural element when the cMUT 100 is inserted into the accommodation groove 210 in the flip chip bonding process, the length and width of the separation groove 220 arranged at the jig 200 has a second margin m2 (e.g., m2 is tens of micrometers (μm)) with respect to the length and width of the thin film forming region M of the cMUT 100.

Although FIGS. 3A and 3B illustrate that two cMUTs are installed at a single jig, a single cMUT may be installed at a single jig or at least three cMUTs may be installed at a single jig.

Hereinafter, a method of manufacturing the jig according to the embodiment will be described in detail with reference to FIGS. 4 and 5A through 5I.

Figure 4:
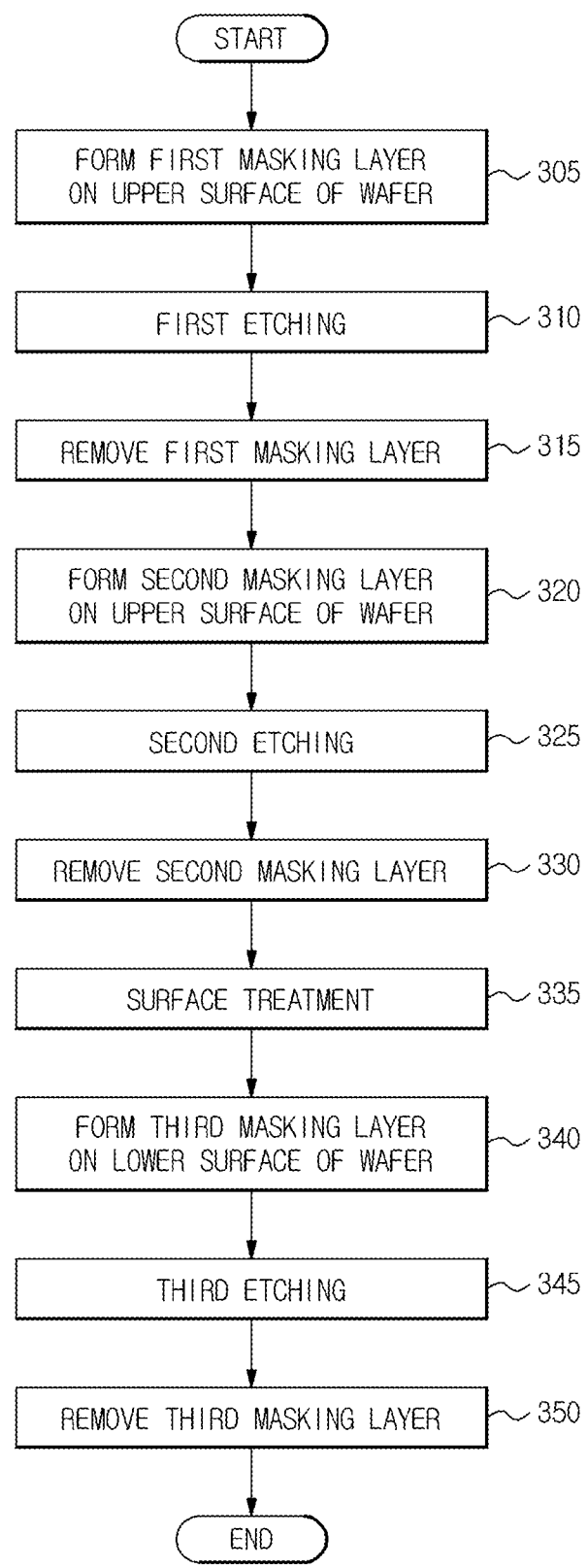
FIG. 4 is a flowchart illustrating a jig manufacturing method according to an embodiment.

FIG. 4 is a flowchart illustrating a jig manufacturing method according to an embodiment. FIGS. 5A through 5I are sectional views explaining the jig manufacturing method according to the embodiment. For convenience of explanation and schematic illustration of drawings, a method of manufacturing a structure in which a single cMUT is installed at a single jig is illustrated in FIGS. 5A through 5I.

Figure 5A:
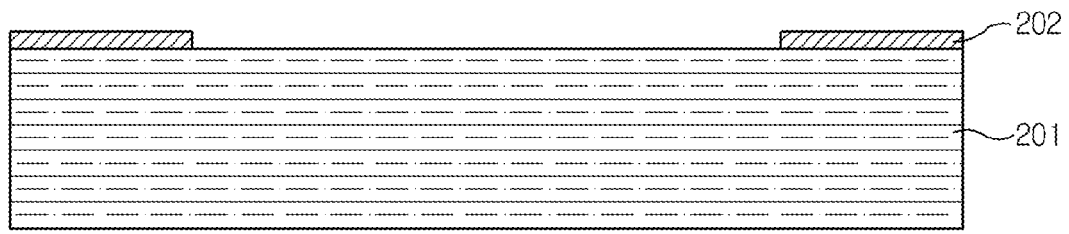
FIGS. 5A through 5I are sectional views for explaining the jig manufacturing method according to an embodiment.

First, a first masking layer 202 is formed on the wafer 201 (operation 305, see FIG. 5A). In this regard, the wafer 201 for forming the jig 200 may be a silicon (Si) wafer, a glass wafer, a replica thereof, or a wafer made of any material allowing an etching process.

Formation of the first masking layer 202 on the wafer 201 will now be described in further detail. First, a photoresist is coated over an upper surface of the wafer 201 (PR coating process). Subsequently, the photoresist is selectively irradiated with light (predominantly, ultraviolet light) using a first mask having desired patterns (exposure process). The desired patterns are formed in the first mask such that the length and width of a region (i.e., accommodation groove) formed by etching using the first masking layer 202 formed through the patterns of the first mask as an etching blocking layer have the first margin m1 (e.g., m1 is 5 to 10 μm) with respect to the length and width of the cMUT 100. In addition, in this process (a first etching process to form the accommodation grooves 210), a pattern to allow the tweezers loading area 240 to be disposed adjacent to the accommodation groove 210 is further formed in the first mask. The first masking layer 202 formed using the first mask having the pattern to form the tweezers loading area 240 is used as an etching blocking layer to form the accommodation groove 210 and the tweezers loading area 240 at the wafer 201.

Thereafter, portions of the photoresist which receive light are removed using a developer to form a pattern on the wafer 201 (developing process). When a positive resist is used as the photoresist, portions of the photoresist which receive light are degraded or softened by light and then removed with a developer, and portions of the photoresist which do not receive light are cured. That is, portions of the photoresist which correspond to the patterns of the first mask remain. The photoresist portions remaining on the wafer 201 through the developing process form the first masking layer 202.

Alternatively, before coating the photoresist on the upper surface of the wafer 201, silicon oxide ($SiO_2$) may be coated over the upper surface of the wafer 201 to form a silicon oxide film layer. Thereafter, the resulting wafer 201 is subjected to the PR coating process, exposure process and developing process and, consequently, photoresist portions corresponding to the patterns of the first mask remain. Next, the silicon oxide film layer is etched using the remaining photoresist portions and the photoresist portions remaining on the silicon oxide film layer are removed and thus the silicon oxide film layer remaining on the wafer 201 is formed as the first masking layer 202.

Figure 5B:
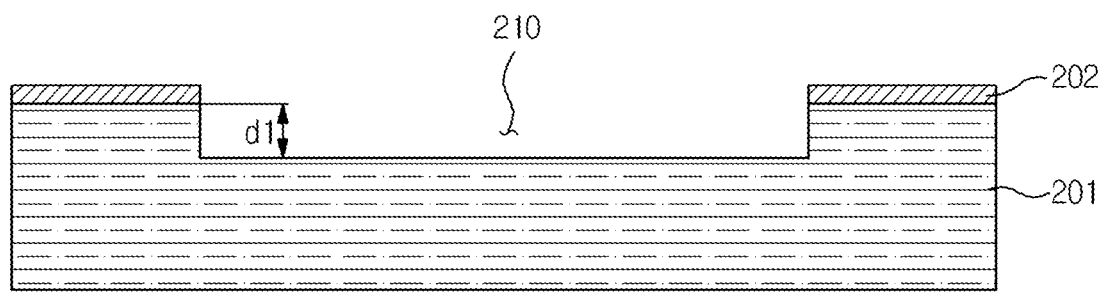

Next, first etching is performed using the first masking layer 202 as an etching blocking layer (operation 310, see FIG. 5B). In this regard, the wafer 201 is etched to a first predetermined depth d1 (e.g., d1 is tens to hundreds of micrometers (μm)) by deep reactive-ion etching (DRIE) to form the accommodation groove 210 to accommodate the cMUT 100 in the wafer 201. When the first etching is performed using as an etching blocking layer the first masking layer 202 formed using the first mask further having the pattern to form the tweezers loading area 240, the accommodation groove 210 and the tweezers loading area 240 disposed adjacent to the accommodation groove 210 are formed in the wafer 201. When the tweezers loading area 240 is formed in the first etching process, provided that an etching depth to form the tweezers loading area 240 at the wafer 201 denotes a third predetermined depth d3, the depth of the accommodation groove 210, i.e., the first predetermined depth d1, is the same as the depth of the tweezers loading area 240, i.e., the third predetermined depth d3 (d1=d3).

Figure 5C:
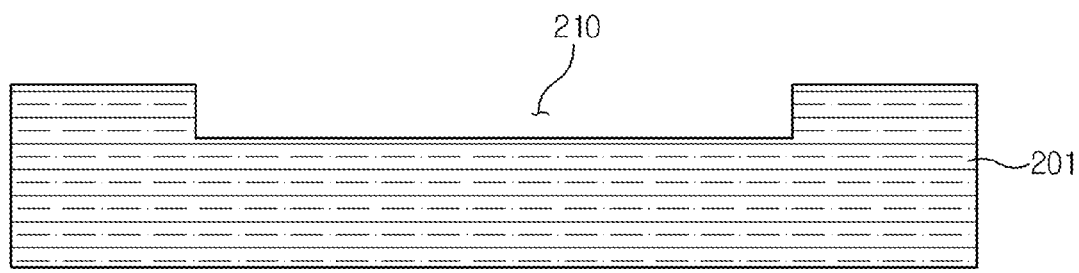

Subsequently, the first masking layer 202 is removed (operation 315, see FIG. 5C).

Figure 5D:
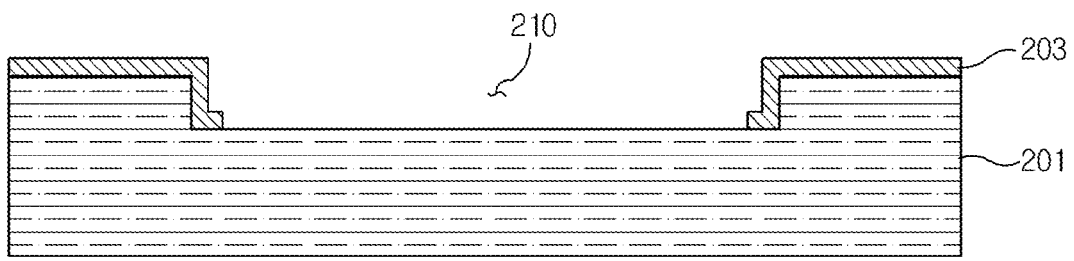

Next, a second masking layer 203 is formed on an upper surface of the wafer 201 from which the first masking layer 202 has been removed (operation 320, see FIG. 5D).

Formation of the second masking layer 203 on the upper surface of the wafer 201 from which the first masking layer 202 has been removed will be described in further detail. First, a photoresist is coated over the upper surface of the wafer 201 (PR coating). Subsequently, the photoresist is selectively irradiated with light (mainly, ultraviolet light) using a second mask having a desired pattern (exposure process). In this regard, the desired pattern is formed in the second mask such that the length and width of a region (i.e., separation groove) formed by etching using the second masking layer 203 formed through the pattern of the second mask as an etching blocking layer have a second margin m2, where m2 is tens of micrometers with respect to the length and width of the thin film forming region M of the cMUT 100. In this regard, the width of the pattern of the second mask is larger than that of the pattern of the first mask. In addition, in this process (second etching to form the separation grooves 220), a pattern may be further formed in the second mask to allow the tweezers loading area 240 to be disposed adjacent to the accommodation groove 210. The second masking layer 203 formed using the second mask having the pattern to form the tweezers loading area 240 is used as an etching blocking layer to form the separation groove 220 and the tweezers loading area 240 at the wafer 201. Subsequently, portions of the photoresist which receive light are removed using a developer to form a pattern on the wafer 201 (developing process). When a positive resist is used as the photoresist, portions of the photoresist which receive light are degraded or softened by light and then removed with a developer, and portions of the photoresist which do not receive light are cured. That is, portions of the photoresist which correspond to the patterns of the second mask remain. The photoresist portions remaining on the wafer 201 through the developing process form the second masking layer 203.

Alternatively, before coating the photoresist on the upper surface of the wafer 201, silicon oxide ($SiO_2$) is coated over the upper surface of the wafer 201 to form a silicon oxide film layer. Thereafter, the resulting wafer 201 is subjected to the PR coating process, exposure process and developing process and, consequently, photoresist portions corresponding to the patterns of the second mask remain. Next, the silicon oxide film layer is etched using the remaining photoresist portions and the photoresist portions remaining on the silicon oxide film layer are removed and thus the silicon oxide film layer remaining on the wafer 201 is formed as the second masking layer 203.

Figure 5E:
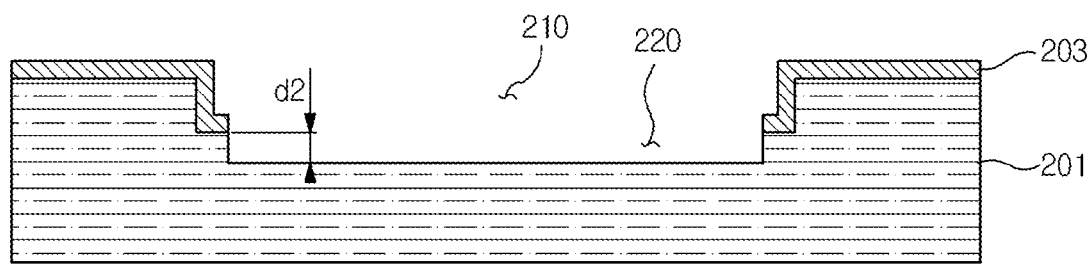

Next, second etching is performed using the second masking layer 203 as an etching blocking layer (operation 325, see FIG. 5E). In this regard, the wafer 201 is etched by DRIE to a second predetermined depth d2, where d2 is tens of micrometers based on an etched plane (i.e., a bottom surface of the accommodation groove 210) of the wafer 201 formed by the first etching process, to form the separation groove 220 that allows the thin films 150 of the cMUT 100 to be present in an empty space without contacting any structural element when the cMUT 100 is inserted into the accommodation groove 210 of the wafer 201. Through formation of the accommodation groove 210 and the separation groove 220 by the first and second etching processes, the seating ends 215 to seat the cMUT 100 are also formed. When the second etching process is performed using as an etching blocking layer the second masking layer 203 formed using the second mask further having a pattern to form the tweezers loading area 240, the tweezers loading area 240 as well as the separation groove 220 is also formed at the wafer 201 to be adjacent to the accommodation loading area 210. When the tweezers loading area 240 is formed in the second etching process, provided that an etching depth to form the tweezers loading area 240 at the wafer 201 denotes a third predetermined depth d3, the depth of the separation groove 220, i.e., the second predetermined depth d2, is the same as the depth of the tweezers loading area 240, i.e., the third predetermined depth d3 (d2=d3).

Alternatively, a pattern to form the tweezers loading area 240 to be adjacent to the accommodation groove 210 may be further formed in both the first mask and the second mask. In this regard, when the first etching process is performed using as an etching blocking layer the first masking layer 202 formed using the first mask further having the pattern to form the tweezers loading area 240 and the second etching process is performed using as an etching blocking layer the second masking layer 203 formed using the second mask further having the pattern to form the tweezers loading area 240, the tweezers loading area 240, in addition to the accommodation groove 210 and the separation groove 220, is also formed at the wafer 201 to be adjacent to the accommodation groove 210. When the tweezers loading area 240 is formed through the first and second etching processes, provided that an etching depth for the formation of the tweezers loading area 240 at the wafer 201 denotes a third predetermined depth d3, a sum (i.e., d1+d2) of the depth (i.e., first predetermined depth d1) of the accommodation groove 210 and the depth (i.e., second predetermined depth d2) of the separation groove 220 is the same as the depth of the tweezers loading area 240, i.e., the third predetermined depth d3 (i.e., d1+d2=d3).

Figure 5F:
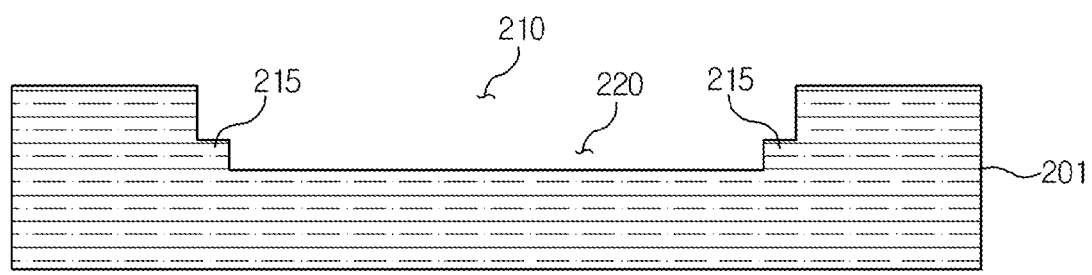

Thereafter, the second masking layer 203 is removed (operation 330, see FIG. 5F).

Next, surface treatment to smooth surfaces (i.e., side and bottom surfaces) of the accommodation groove 210 and the separation groove 220 formed through the first and second etching processes, i.e., smoothing treatment to remove roughness of the surfaces of the accommodation groove 210 and the separation groove 220 is performed (operation 335). In this regard, the surface treatment to obtain smooth surfaces may be performed using tetramethyl ammonium hydroxide (TMAH) dipping treatment, KOH dipping treatment, or plasma treatment.

In this regard, after manufacturing the jig 200 through which the vacuum holes 230 are not formed, by performing operation 305 to operation 335 (see FIG. 5F) of FIG. 4, the cMUT 100 may be installed at the jig 200 and then flip chip bonding may be performed thereon. In addition, the jig 200 with a plurality of vacuum holes 230 formed therein may be manufactured by performing operation 305 to operation 350 of FIG. 4.

Figure 5G:
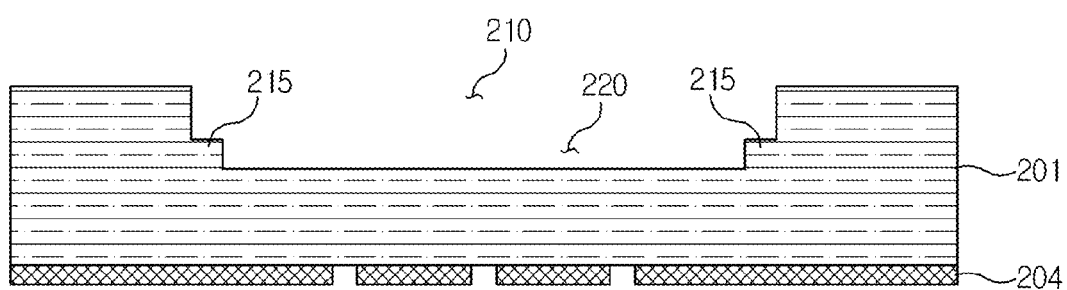

After operation 335 of FIG. 4, a third masking layer 204 is formed on a lower surface of the wafer 201, from which the second masking layer 203 has been removed (operation 340, see FIG. 5G).

Formation of the third masking layer 204 on the lower surface of the wafer 201 from which the second masking layer 203 will be described in further detail. First, a photoresist is coated over the lower surface of the wafer 201 (PR coating). Subsequently, the photoresist is selectively irradiated with light (mainly, ultraviolet light) using a second mask having a desired pattern (exposure process). The desired pattern is formed in the third mask so that vacuum pressure applied through a plurality of holes (i.e., vacuum holes) formed by performing etching using as an etching blocking layer the third masking layer 204 formed by the pattern formed in the third mask is uniformly applied over the thin films 150. Thereafter, portions of the photoresist which receive light are removed using a developer to form a pattern on the wafer 201 (developing process). When a positive resist is used as the photoresist, portions of the photoresist which receive light are degraded or softened by the light and then removed using a developer, and portions of the photoresist which do not receive light are cured. That is, portions of the photoresist corresponding to the pattern of the third mask remain. The photoresist portions remaining on the wafer 201 through the developing process form the first masking layer 204.

Alternatively, before coating the photoresist on the lower surface of the wafer 201, silicon oxide ($SiO_2$) is coated over the lower surface of the wafer 201 to form a silicon oxide film layer. Thereafter, the resulting wafer 201 is subjected to the PR coating process, exposure process and developing process and, consequently, photoresist portions corresponding to the pattern of the third mask remain. Next, the silicon oxide film layer is etched using the remaining photoresist portions and the photoresist portions remaining on the silicon oxide film layer are removed and thus the silicon oxide film layer remaining on the wafer 201 is formed as the third masking layer 204.

Figure 5H:
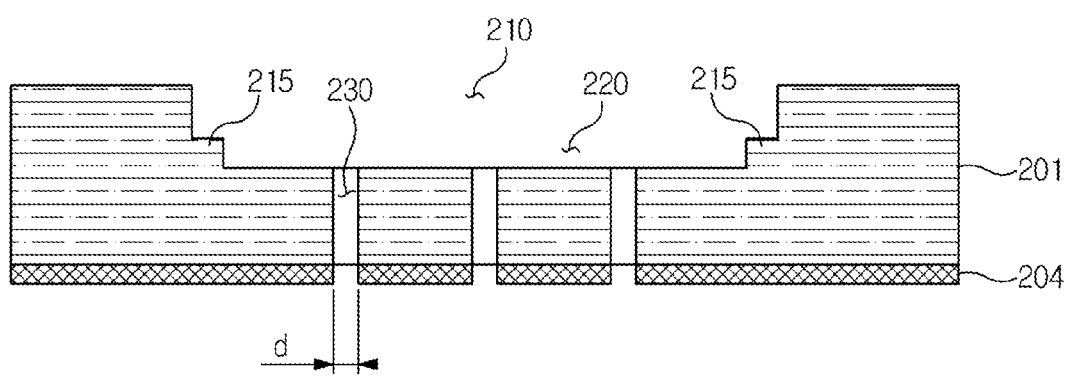

Next, third etching is performed using the third masking layer 204 as an etching blocking layer (operation 345, see FIG. 5H). The third etching process is to form the vacuum holes 230 in the wafer 201 to penetrate the wafer 201, and the vacuum holes 230 may have various shapes, such as a prism shape (generally, a square pillar shape), a cylindrical shape, and the like. In this regard, the vacuum holes 230 having a certain length and a certain width (or a certain diameter) that is sufficient to apply vacuum pressure to the thin films 150 of the cMUT 100 during flip chip bonding are formed by etching (i.e., DRIE) to penetrate the wafer 201 to a predetermined width or diameter d (here, d is a predetermined width when the vacuum holes have a square pillar shape, d is a predetermined diameter when the vacuum holes have a cylindrical shape, and d ranges from tens to hundreds of micrometers).

In the present embodiment, the third masking layer 204 is formed on the lower surface of the wafer 201. In another embodiment, however, the vacuum holes 230 may be formed in the wafer 201 by forming, on an upper surface of the wafer 201 on which the second etching process has been performed, the third masking layer 204 to form the vacuum holes 230 having a certain length and a certain width, and performing third etching using the third masking layer 204 as an etching blocking layer.

Figure 5I:
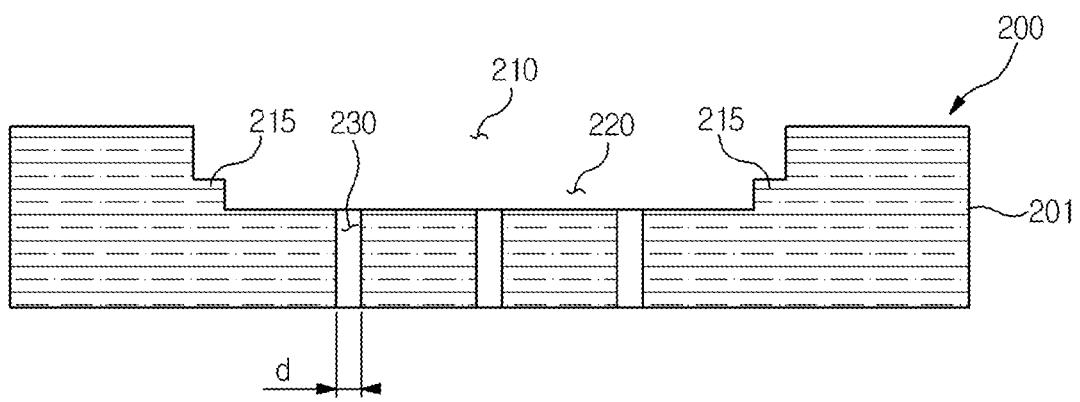

Subsequently, the third masking layer 204 is removed, thereby completing manufacture of the jig 200 through which the vacuum holes 230 are formed (operation 350, see FIG. 5I).

The jig 200 according to the embodiment is manufactured using a semiconductor manufacturing process and thus a fabrication error (machining error) is just several micrometers. Thus, machining accuracy is very high. Such high machining accuracy is applied when flip chip bonding between semiconductor chips is performed using the jig 200 and thus may improve bonding accuracy.

Figure 6:
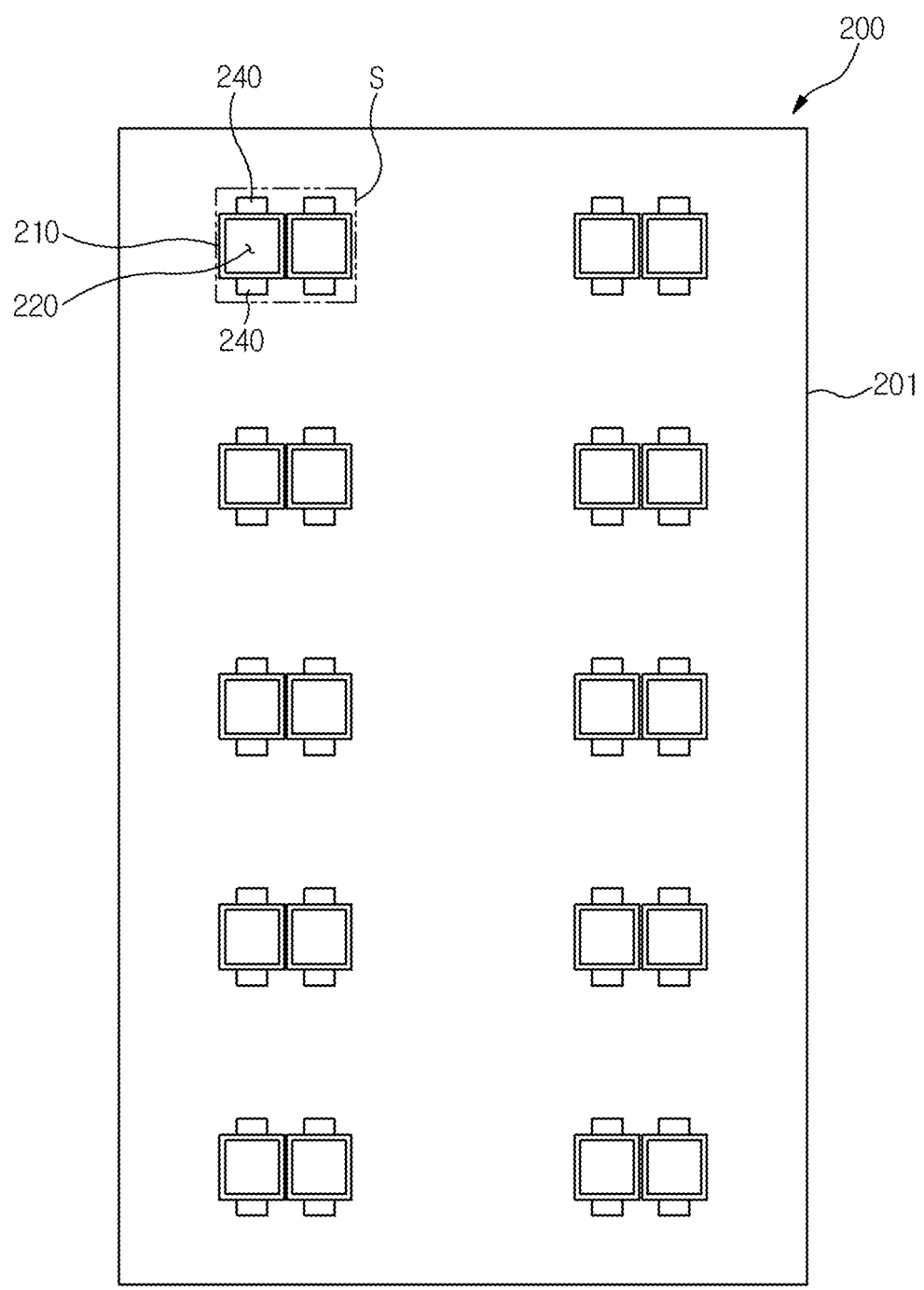
FIG. 6 is a diagram for explaining a case in which structures enabling bonding in a 1:n manner are formed as an array at a single jig.

FIG. 6 is a diagram for explaining a case in which structures enabling bonding in a 1:n manner are formed as an array at a single jig.

In FIG. 6, structures S are formed as a 5×2 array, wherein each structure S enables bonding in a 1:2 manner, i.e., structures in which two accommodation grooves 210 (separation grooves 220 are formed) to seat two cMUTs 100 in parallel are positioned in parallel at the jig 200 and two tweezers loading areas 240 to load tweezers to pick up the cMUT 100 when the cMUT 100 is installed at the jig 200 are formed for the respective accommodation grooves 210.

In such a manner, structures enabling bonding in a 1:1 or 1:n manner are repeatedly formed at the jig 200, the cMUTs 100 are installed at each structure (including accommodation grooves 210 and separation grooves 220), alignment between an integrated circuit and cMUTs 100 installed at the jig 200 is consecutively performed, and flip chip bonding may be performed between a relatively large number of cMUTs 100 and the jig 200 through single reflow treatment. Accordingly, yield and throughput may be improved and uniformity of bonded chips may also be improved.

In addition, FIG. 6 illustrates that structures enabling one type of bonding (i.e., structures enabling bonding in a 1:2 manner) are repeatedly formed at the jig 200. In another embodiment, however, structures enabling several types of bonding in a 1:n manner (e.g., structures enabling bonding in a 1:1 manner, 1:2 manner, and the like) may be formed at the jig 200 as an array.

Hereinafter, a flip chip bonding method of chips for an ultrasound probe using the jig according to the above-described embodiment will be described in detail with reference to FIGS. 7 and 8A through 8E.

Figure 7:
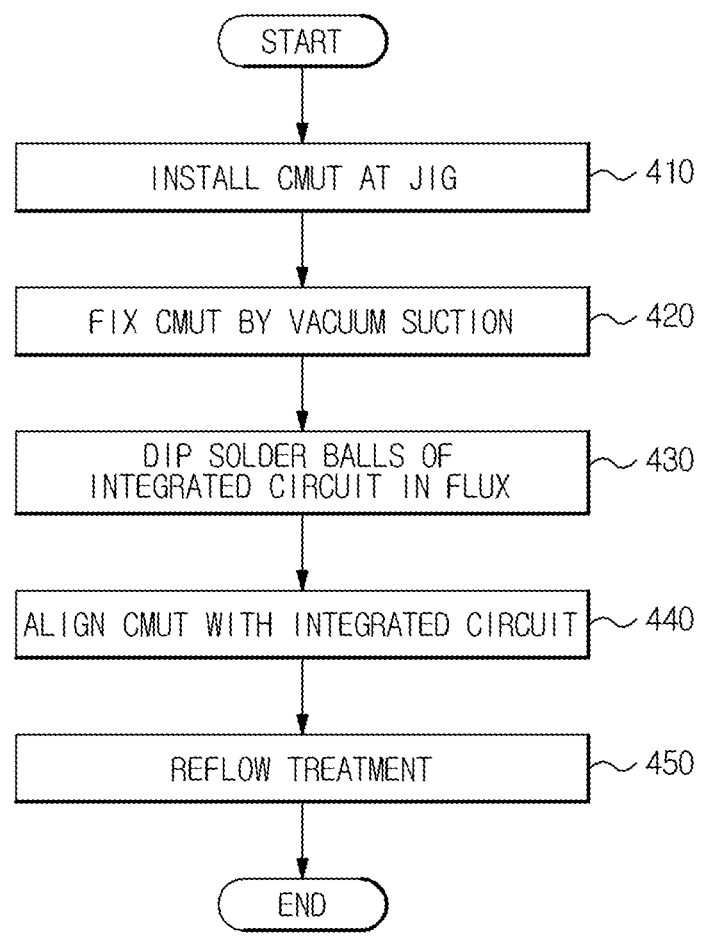
FIG. 7 is a flowchart illustrating a flip chip bonding method of chips for an ultrasound probe using a jig, according to an embodiment.

FIG. 7 is a flowchart illustrating a flip chip bonding method of chips for an ultrasound probe using a jig, according to an embodiment. FIGS. 8A through 8E are sectional views for explaining the flip chip bonding method according to the embodiment. FIGS. 8A through 8E illustrate installation of two cMUTs 100 at the jig 200 with no vacuum holes formed therethrough and flip chip bonding between the two cMUTs 100 and an integrated circuit 600.

Figure 8A:
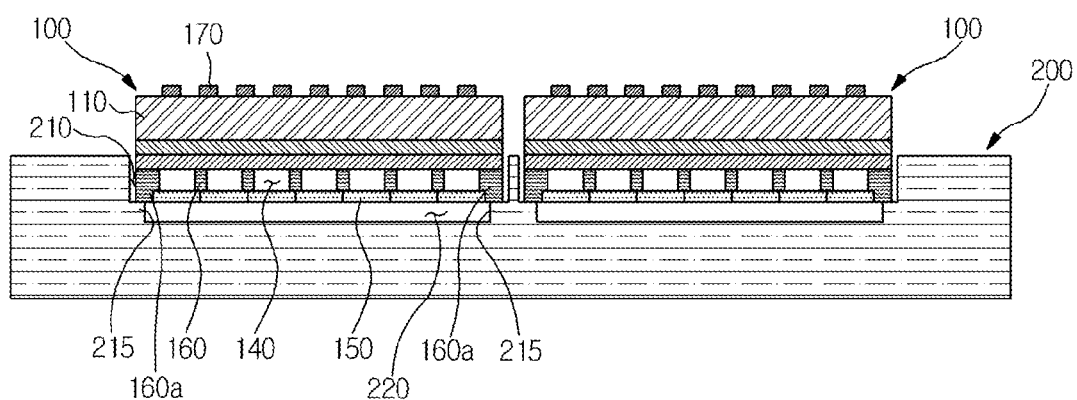
FIGS. 8A through 8E are sectional views for explaining the flip chip bonding method according to the embodiment.

First, the cMUTs 100 are installed at the jig 200 (operation 410, see FIG. 8A). That is, as illustrated in FIG. 8A, the cMUTs 100 are installed at the respective accommodation grooves 210 of the jig 200 such that a surface of each of the cMUTs 100 on which the bonding pads 170 are formed faces up and the thin films 150 of each of the cMUTs 100 face down.

Figure 8B:
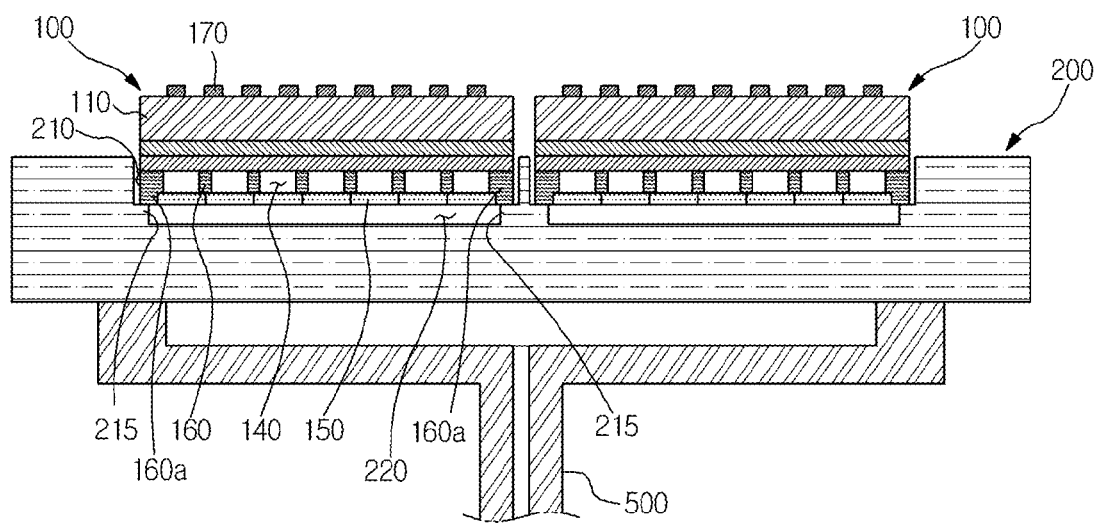
Figure 8C:
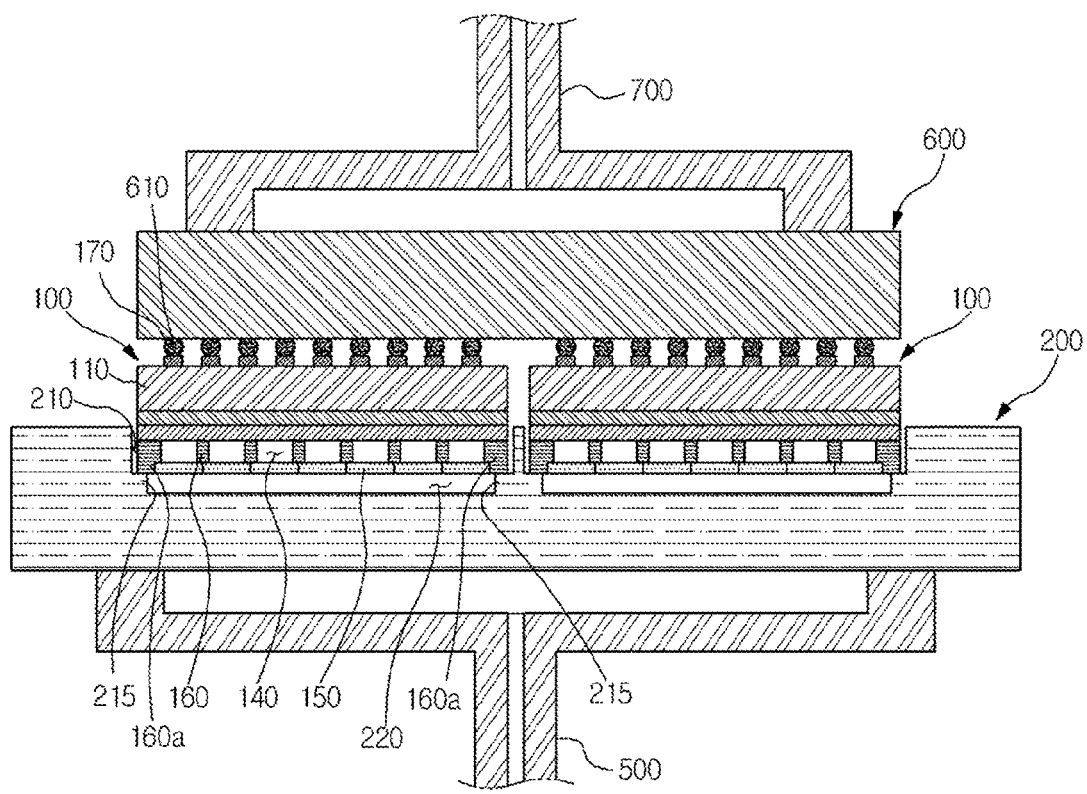
Figure 8D:
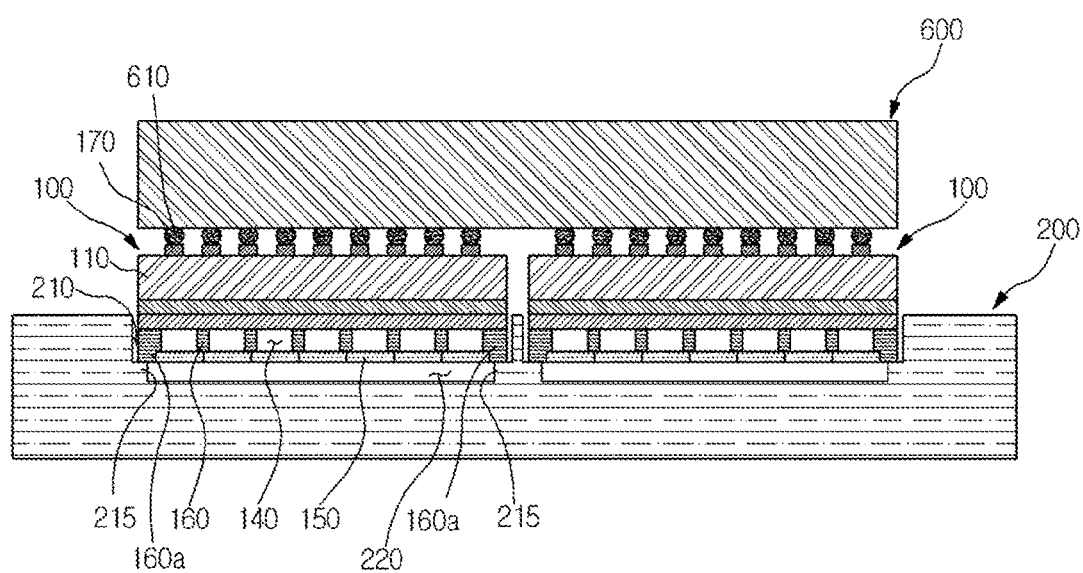

Next, a lower surface of the jig 200 is vacuum-suctioned using a vacuum suction device 500 to fix the cMUTs 100 accommodated at the jig 200 (operation 420, see FIG. 8B).

As described above, when the cMUTs 100 generally have a rectangular shape, the length and width of the accommodation grooves 210 arranged at the jig 200 are formed to have a very small margin, e.g., about 5 to 10 µm with respect to the length and width of the cMUTs 100. Thus, the cMUTs 100 may be fitted into the respective accommodation grooves 210 of the jig 200. Accordingly, as illustrated in FIGS. 8A and 8B, in the flip chip bonding process, even though the lower surface of the jig 200 is suctioned using the vacuum suction device 500 after installing the cMUTs 100 at the jig 200 with no vacuum holes 230, the position of the cMUTs 100 accommodated at the jig 200 is rigidly fixed, which enables flip chip bonding between the cMUTs 100 and the integrated circuit 600.

Subsequently, a surface of the integrated circuit 600 on which solder balls 610 are not formed is vacuum-suctioned using a vacuum suction device 700 and a flux is coated on the solder balls 610 formed on the integrated circuit 600 (operation 430). Thereafter, the integrated circuit 600 and the cMUTs 100 are pre-adhered by aligning the integrated circuit 600 with the cMUTs 100 in a state in which the integrated circuit 600 is vacuum-suctioned, so that the solder balls 610 of the integrated circuit 600 contact the bonding pads 170 of the cMUTs 100 (operation 440, see FIG. 8C).

An alignment error generated when aligning the integrated circuit 600 with the cMUTs 100 coincides with a fabrication error generated when the jig 200 is manufactured, and thus bonding accuracy may be improved when flip chip bonding is performed between the cMUTs 100 installed at the jig 200 and the integrated circuit 600.

Figure 8E:
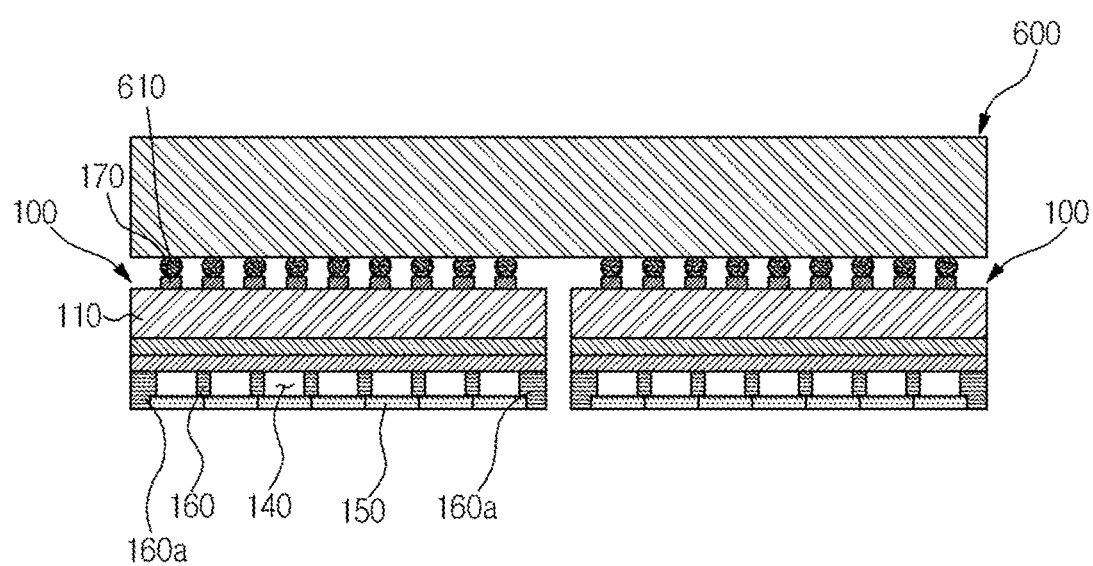

Next, the vacuum suction devices 500 and 700 that suction and fix the jig 200 and the integrated circuit 600 are removed, and the solder balls 610 formed on the integrated circuit 600 are adhered to the bonding pads 170 formed on the cMUTs 100 by performing a reflow process on the cMUTs 100 and the integrated circuit 600 that have been pre-adhered to one another, thereby completing flip chip bonding between the cMUTs 100 and the integrated circuit 600 (operation 450, see FIG. 8E).

FIGS. 9A through 9E are sectional views for explaining a flip chip bonding method of chips for an ultrasound probe using a jig, according to another embodiment.

As illustrated in FIGS. 9A through 9E, the flip chip bonding method of chips for an ultrasound probe using the jig according to another embodiment is different from the flip chip bonding method of chips for an ultrasound probe using the jig according to an embodiment as illustrated in FIGS. 7 and 8A through 8E in that cMUTs 100 are installed at a jig 200 through which a plurality of vacuum holes 230 is formed and flip chip bonding is performed between the cMUTs 100 and an integrated circuit 600.

Figure 9A:
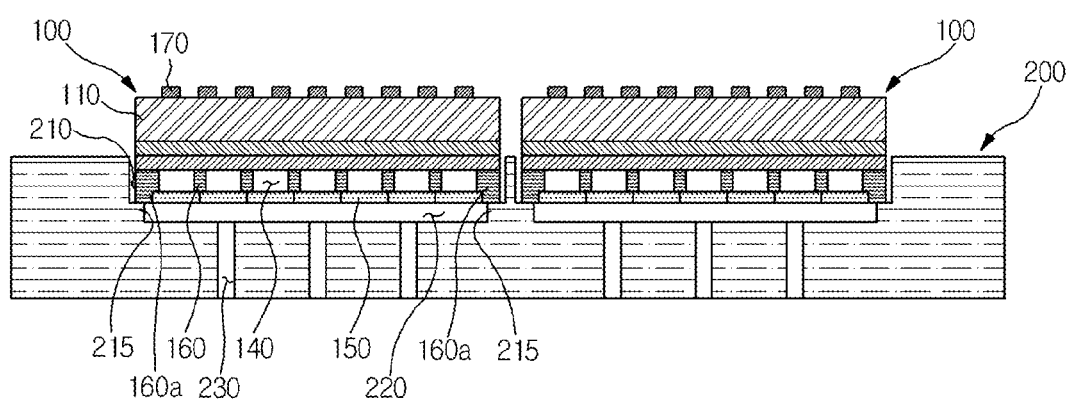
FIGS. 9A through 9E are sectional views for explaining a flip chip bonding method of chips for an ultrasound probe using a jig, according to another embodiment.
Figure 9B:
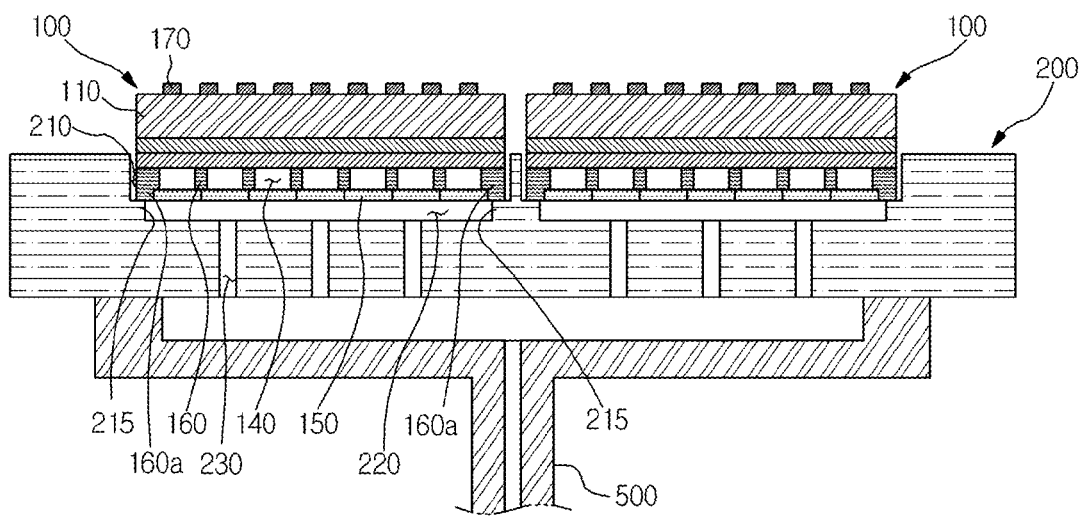
Figure 9C:
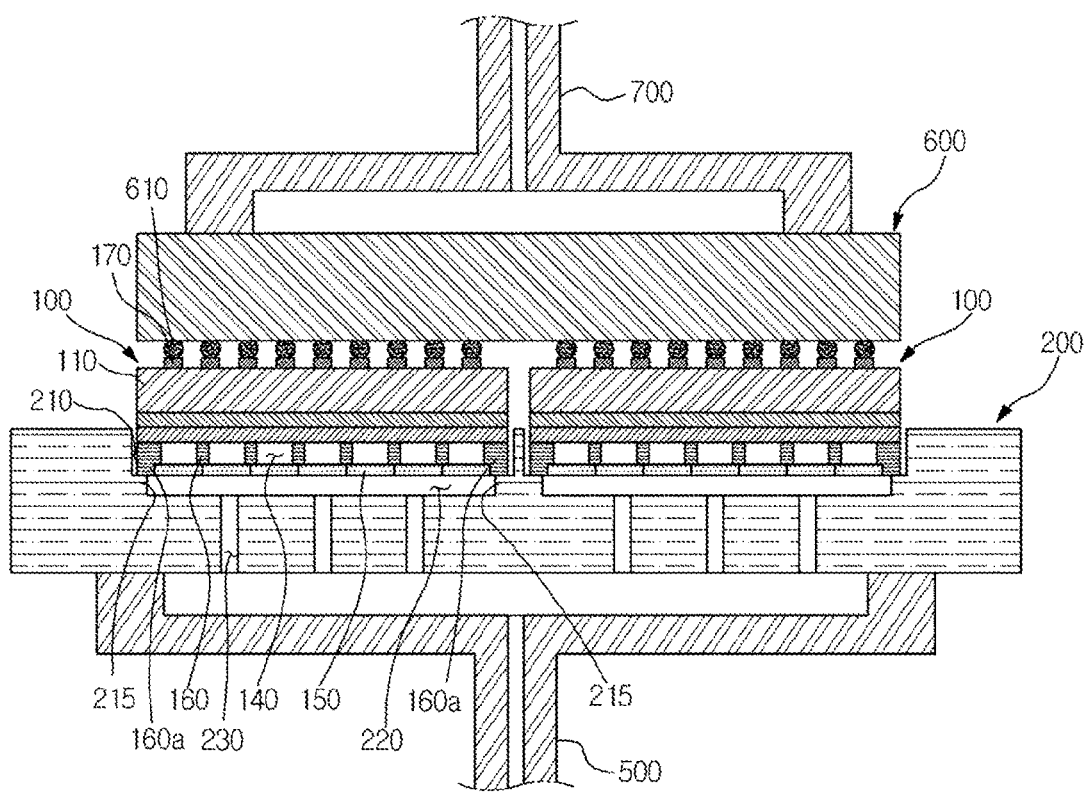
Figure 9D:
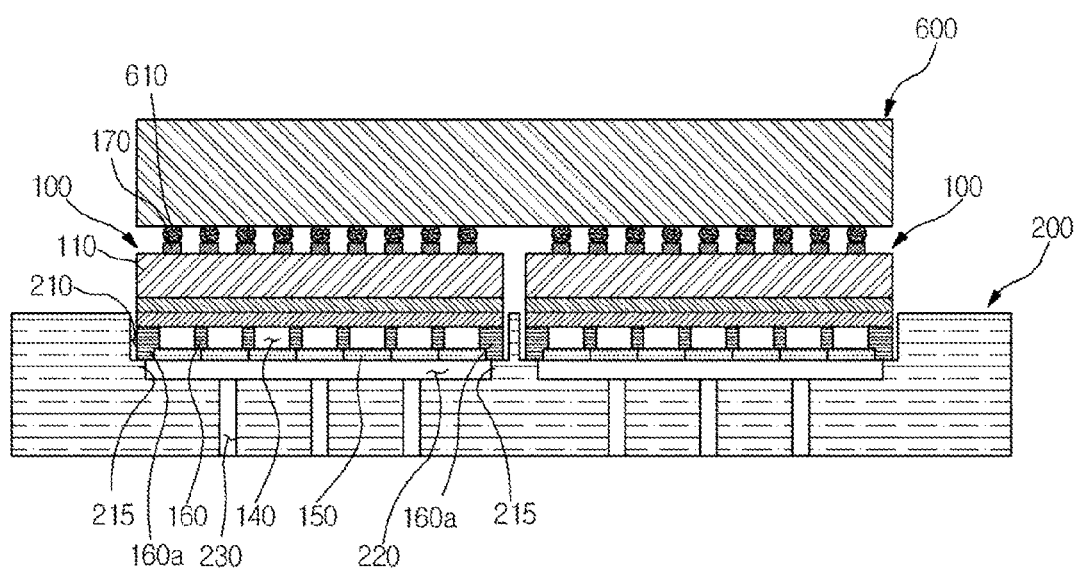
Figure 9E:
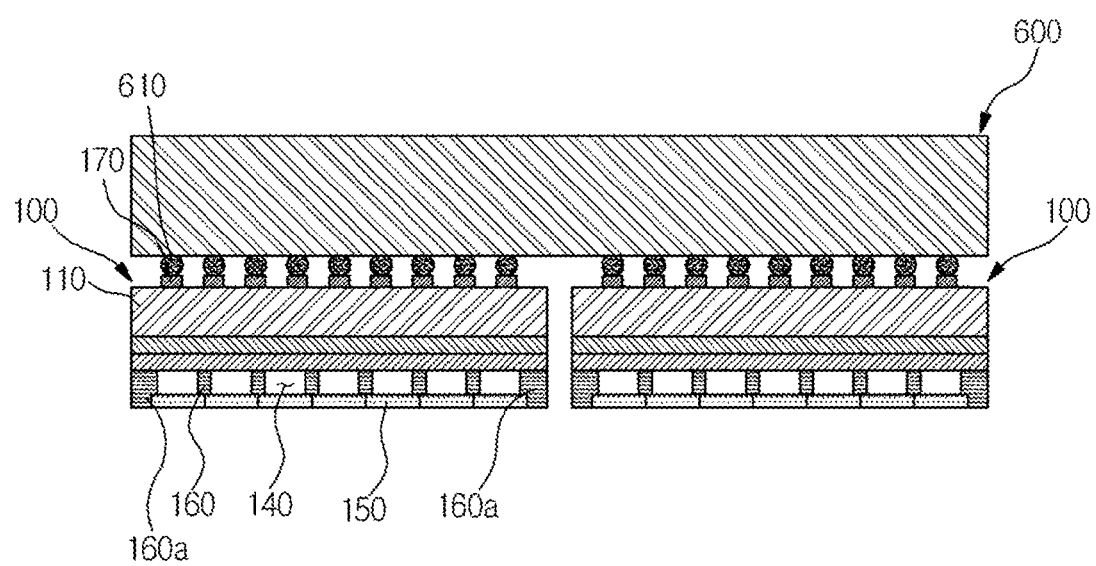

That is, unlike the case in which the cMUTs 100 are fixed by vacuum suction as described in operation 420 of FIG. 7, in the present embodiment, the cMUTs 100 are indirectly vacuum-suctioned by applying vacuum pressure generated from a vacuum suction device 500 to thin films 150 of each of the cMUTs 100 through the vacuum holes 230 formed through the jig 200 to fix the cMUTs 100 accommodated at the jig 200 (operation 420, see FIG. 9B). In this regard, the vacuum pressure applied through the vacuum holes 230 is uniformly applied over the thin films 150 of the cMUT 100, and thus damage to the thin films 150 of the cMUT 100 caused by direct contact between the thin films 150 and the vacuum suction device 500 may be reduced.

In the flip chip bonding method illustrated in FIGS. 9A through 9E, other processes are the same as the flip chip bonding processes of chips for an ultrasound probe using the jig according to an embodiment illustrated in FIGS. 8A through 8E, except that the cMUTs 100 are installed at the jig 200 through which the vacuum holes 230 are formed and the cMUTs 100 are indirectly vacuum-suctioned by transfer of vacuum pressure via the vacuum holes 230 to fix the cMUTs 100 accommodated at the jig 200. Thus, a detailed description thereof will be omitted.

As is apparent from the above description, according to a jig, a manufacturing method thereof, and a flip chip bonding method of chips for an ultrasound probe using the jig, a jig to stably seat a semiconductor chip to be flip-chip bonded with a single semiconductor chip is manufactured, the semiconductor chip is seated at the jig, and then flip chip bonding is performed therebetween. Thus, damage to the semiconductor chip including structures on opposite surfaces thereof which may be caused during flip chip bonding may be prevented.

In addition, according to a jig, a manufacturing thereof, and a flip chip bonding method of chips for an ultrasound probe using the jig, a jig to stably seat a plurality of semiconductor chips to be flip-chip bonded with a single semiconductor chip is manufactured, the semiconductor chips are seated at the jig, and flip chip bonding is performed therebetween, and thus a degree of freedom of fabrication may be improved in bonding between the single semiconductor chip and the plurality of semiconductor chips (i.e., it may be possible to perform bonding in a 1:n manner).

Moreover, according to a jig, a manufacturing method thereof, and a flip chip bonding method of chips for an ultrasound probe using the jig, a jig to stably seat a semiconductor chip(s) to be flip-chip bonded with a single semiconductor chip is manufactured using a semiconductor manufacturing process. Thus bonding accuracy may be improved when flip chip bonding is performed between the semiconductor chips.

Furthermore, according to a jig, a manufacturing method thereof, and a flip chip bonding method of chips for an ultrasound probe using the jig, a jig including structures enabling bonding in a 1:1 or 1:n manner that are formed as an array is manufactured, a relatively large number of semiconductor chips are seated at the jig, alignment between a single semiconductor chip and the semiconductor chips is consecutively performed, and reflow treatment is performed once Thus, yield and throughput may be improved.

Although a few exemplary embodiments have been shown and described, it would be appreciated by those skilled in the art that changes may be made in these embodiments without departing from the principles and spirit of the inventive concept, the scope of which is defined in the claims and their equivalents.

What is claimed is:
1. A jig comprising:
   a wafer comprising:
      an accommodation groove configured to accommodate a capacitive micromachined ultrasonic transducer (cMUT) when flip chip bonding is performed; and
      a separation groove formed in a bottom surface of the accommodation groove, the separation groove having a bottom surface that is spaced apart from thin films of the cMUT that face the bottom surface of the separation groove when the cMUT is seated on portions of the bottom surface of the accommodation groove.

2. The jig according to claim 1, wherein the accommodation groove has a first predetermined depth, and the separation groove has a second predetermined depth from the bottom surface of the accommodation groove.

3. The jig according to claim 2, wherein the accommodation groove has a length and a width which are larger than a length and a width of the cMUT, respectively.

4. The jig according to claim 3, wherein the separation groove has a length and a width which are larger than a length and a width of a thin film forming region of the cMUT, respectively, and are smaller than the length and the width of the cMUT, respectively.

5. The jig according to claim 2, wherein the wafer further comprises a tweezers loading area disposed adjacent to the accommodation groove and configured to allow tweezers to pick up the cMUT when the cMUT is accommodated in the accommodation groove
wherein the tweezers loading area is formed in the wafer to have a third predetermined depth.

6. The jig according to claim 1, wherein the wafer is any one of a silicon (Si) wafer, a glass wafer, and a replica using the Si wafer or the glass wafer.

7. The jig according to claim 1, wherein the wafer further comprises a plurality of vacuum holes formed below the separation groove and through which vacuum pressure is applied to the thin films of the cMUT when the flip chip bonding is performed.

8. A jig comprising:
a wafer comprising:
an accommodation groove configured to accommodate a capacitive micromachined ultrasonic transducer (cMUT) when flip chip bonding is performed; and
seating ends provided in a bottom surface of the accommodation groove and configured to seat the cMUT within the accommodation groove so that thin films of the cMUT are spaced apart from and face an etched portion of the bottom surface of the accommodation groove face when the flip chip bonding is performed.

9. A jig comprising:
a wafer comprising:
accommodation grooves configured to accommodate a plurality of capacitive micromachined ultrasonic transducers (cMUTs) when flip chip bonding is performed; and
a plurality of separation grooves formed bottom surfaces of the accommodation grooves, each of the separation grooves having a bottom surface that is spaced apart from thin films of a respective cMUT that face the bottom surface of the separation groove when the cMUTs are seated on portions of the bottom surfaces of the accommodation grooves.

10. A jig comprising:
a wafer comprising:
an accommodation groove configured to accommodate a capacitive micromachined ultrasonic transducer (cMUT) when flip chip bonding is performed; and
a separation groove formed below the accommodation groove and configured to protect thin films of the cMUT.

11. The jig according to claim 10, wherein the accommodation groove has a first predetermined depth, and the separation groove has a second predetermined depth from the bottom surface of the accommodation groove.

12. A jig comprising:
a wafer comprising:
an accommodation groove configured to accommodate an ultrasound transducer when flip chip bonding is performed; and
a separation groove formed in a bottom surface of the accommodation groove, the separation groove having a bottom surface that is spaced apart from the ultrasound transducer when the ultrasound transducer is seated on portions of the bottom surface of the accommodation groove.

* * * * *